(12) United States Patent
Zhang

(10) Patent No.: US 9,050,420 B2
(45) Date of Patent: Jun. 9, 2015

(54) DEVICE AND METHOD FOR MONITORING A VASCULAR ACCESS FOR AN EXTRACORPOREAL BLOOD TREATMENT

(75) Inventor: Wei Zhang, Niederwerrn (DE)

(73) Assignee: Fresenius Medical Care Deutschland GmbH, Bad Homburg (DE)

(*) Notice: Subject to any disclaimer, the term of this patent is extended or adjusted under 35 U.S.C. 154(b) by 0 days.

(21) Appl. No.: 13/578,306

(22) PCT Filed: Feb. 7, 2011

(86) PCT No.: PCT/EP2011/000560
§ 371 (c)(1),
(2), (4) Date: Sep. 11, 2012

(87) PCT Pub. No.: WO2011/098243
PCT Pub. Date: Aug. 18, 2011

(65) Prior Publication Data
US 2013/0012861 A1    Jan. 10, 2013

(30) Foreign Application Priority Data
Feb. 12, 2010    (DE) .......................... 10 2010 007 914

(51) Int. Cl.
*A61M 1/14*    (2006.01)
*A61M 1/34*    (2006.01)
(Continued)

(52) U.S. Cl.
CPC .......... *A61M 1/3653* (2013.01); *A61B 5/14557* (2013.01); *A61M 2205/14* (2013.01);
(Continued)

(58) Field of Classification Search
CPC ..................... A61M 2205/15; A61M 2205/44; A61M 2001/3656; A61M 1/14; A61M 1/3653; A61M 2001/361; A61M 2205/18; A61M 2205/3306; A61M 1/3639; A61M 1/367; A61M 2039/1005; A61M 1/3656; A61M 2202/0413; A61M 2202/0429; A61M 2202/0433; A61M 2205/14; A61M 2205/33; A61M 2205/3313; A61M 2205/3327; A61B 5/0059; A61B 5/0075; A61B 5/1455; A61B 5/14551; A61B 5/14552; A61B 5/14557; A61B 5/1468; G01N 21/31

USPC ............ 604/6.16, 4.01, 5.01, 6.06, 6.08, 6.1, 604/6.11; 422/44
See application file for complete search history.

(56) References Cited

U.S. PATENT DOCUMENTS 5,382,227 A * 1/1995 Riquier ........................ 604/6.05
6,537,240 B2    3/2003 Cavicchioli et al.
(Continued)

FOREIGN PATENT DOCUMENTS

DE          697 31 943 T2    12/2005
DE    10 2006 032815 A1     1/2008
(Continued)

OTHER PUBLICATIONS

International Preliminary Report on Patentability from PCT/EP2011/000560 mailed on Aug. 14, 2012.
(Continued)

*Primary Examiner* — Adam Marcetich
(74) *Attorney, Agent, or Firm* — Kenyon & Kenyon LLP

(57) ABSTRACT

A device and method for monitoring an access to a patient for an extracorporeal blood treatment apparatus with an extracorporeal blood circuit are described, as well as an extracorporeal blood treatment apparatus with a device for monitoring the vascular access. The device and method are based on the monitoring of a characteristic property of the blood, in particular the concentration of haemoglobin in the blood flowing in the arterial blood line of extracorporeal blood circuit I of an extracorporeal blood treatment apparatus A. In the event of an incorrect vascular access, the flow conditions change in the communicating intra- and extracorporeal blood circulation system. These changes in the flow conditions can be detected as a change in the haemoglobin concentration. A disconnection of venous puncture cannula for the patient access is ascertained by a reduction in the haemoglobin concentration in the blood in arterial blood line.

15 Claims, 2 Drawing Sheets

(51) Int. Cl.
*A61M 1/36* (2006.01)
*A61B 5/1455* (2006.01)
*A61B 5/00* (2006.01)
*A61M 39/10* (2006.01)

(52) U.S. Cl.
CPC ....... *A61M2202/0413* (2013.01); *A61B 5/0059* (2013.01); *A61B 5/14551* (2013.01); *A61B 5/14552* (2013.01); *A61M 2039/1005* (2013.01); *A61B 5/1455* (2013.01); *A61M 2202/0433* (2013.01); *A61M 2202/0429* (2013.01); *A61M 2205/3306* (2013.01); *A61M 2205/33* (2013.01); *A61B 5/0075* (2013.01); *A61M 2205/15* (2013.01); *A61M 2205/18* (2013.01); *A61M 2230/201* (2013.01); *A61M 2230/205* (2013.01); *A61M 2230/207* (2013.01); *A61M 2230/208* (2013.01); *A61M 1/361* (2014.02); *A61M 1/3656* (2014.02)

(56) References Cited

U.S. PATENT DOCUMENTS

| | | | |
|---|---|---|---|
| 6,623,443 B1* | 9/2003 | Polaschegg | 604/5.04 |
| 6,663,585 B1* | 12/2003 | Ender | 604/6.08 |
| 2001/0007930 A1* | 7/2001 | Kleinekofort | 604/4.01 |
| 2002/0062098 A1 | 5/2002 | Cavicchioli et al. | |
| 2003/0036719 A1* | 2/2003 | Giacomelli et al. | 604/5.04 |
| 2003/0128125 A1 | 7/2003 | Burbank et al. | |
| 2003/0138961 A1* | 7/2003 | Fava et al. | 436/66 |
| 2003/0176829 A1* | 9/2003 | Lodi et al. | 604/4.01 |
| 2003/0195454 A1* | 10/2003 | Wariar et al. | 604/5.01 |
| 2004/0129616 A1* | 7/2004 | Mori et al. | 210/85 |
| 2004/0186409 A1* | 9/2004 | Cavalcanti et al. | 604/4.01 |
| 2004/0254513 A1 | 12/2004 | Shang et al. | |
| 2005/0038325 A1 | 2/2005 | Moll | |
| 2007/0078368 A1* | 4/2007 | Felt et al. | 604/4.01 |
| 2007/0112289 A1* | 5/2007 | Cavalcanti et al. | 604/4.01 |
| 2007/0118064 A1* | 5/2007 | Ueda et al. | 604/6.09 |
| 2008/0097272 A1* | 4/2008 | Daniel et al. | 604/6.09 |
| 2009/0082653 A1 | 3/2009 | Rohde | |
| 2009/0088683 A1 | 4/2009 | Roger et al. | |
| 2009/0152200 A1* | 6/2009 | Lannoy | 210/647 |
| 2010/0099964 A1* | 4/2010 | O'Reilly et al. | 600/323 |
| 2010/0145175 A1* | 6/2010 | Soldo et al. | 600/365 |
| 2012/0029410 A1 | 2/2012 | Koenig et al. | |

FOREIGN PATENT DOCUMENTS

| | | |
|---|---|---|
| DE | 10 2009 008 885 A1 | 8/2010 |
| EP | 1 748 292 | 1/2007 |
| WO | 99/29356 | 6/1999 |
| WO | 2006/008866 | 1/2006 |
| WO | 2008/000433 A1 | 1/2008 |
| WO | 2009/065611 | 5/2009 |

OTHER PUBLICATIONS

PCT International Search Report from PCT/EP2011/000560 mailed on Jun. 30, 2011.

* cited by examiner

DEVICE AND METHOD FOR MONITORING A VASCULAR ACCESS FOR AN EXTRACORPOREAL BLOOD TREATMENT

CROSS REFERENCE TO RELATED APPLICATIONS

The present application is the national stage entry of International Patent Application No. PCT/EP2011/000560, filed on Feb. 7, 2011, and claims priority to Application No. DE 10 2010 007 914.6, filed in the Federal Republic of Germany on Feb. 12, 2010.

FIELD OF INVENTION

The present invention relates to a device for monitoring an access to a patient for an extracorporeal blood treatment apparatus with an extracorporeal blood circuit. Moreover, the present invention relates to a method for monitoring a patient access in an extracorporeal blood treatment. The present invention also relates to an extracorporeal blood treatment apparatus with a device for monitoring the vascular access.

BACKGROUND INFORMATION

In the field of medical technology, various extracorporeal blood treatment apparatuses are known which comprise an extracorporeal blood circuit. The known extracorporeal blood treatment apparatuses include for example dialysis apparatuses, which necessitate an access to the vascular system of the patient. In extracorporeal blood treatment, blood is withdrawn from the patient via an arterial hose line with an arterial puncture cannula, the blood being fed back again to the patient via a venous hose line with a venous puncture cannula. Extracorporeal blood treatment apparatuses comprise a blood pump for conveying the blood in the extracorporeal blood circuit.

Despite regular monitoring of the vascular access by hospital staff during extracorporeal blood treatment, there is in principle the risk of the venous puncture cannula slipping out of the patient's blood vessel unnoticed. Whereas slipping-out of the arterial cannula is associated with the sucking-in of air into the arterial hose line, the slipping-out of the venous cannula leads to the feared free flow of blood into the surroundings. If the slipping-out of the venous cannula is not detected immediately, therefore, there is the risk of the patient bleeding to death.

Various devices of differing design are known for the monitoring of the vascular access. The known monitoring devices generally rely on the safety devices which are present as standard in blood treatment apparatuses and which, in the event of an incorrect vascular access, trigger an immediate interruption to the blood flow in the extracorporeal blood circuit.

A monitoring device for a vascular access is described in International Patent Publication No. WO 99/29356 A1, wherein the strength of an electric current flowing through the fluid in the hose line is measured. U.S. Patent Publication No. 2004/0254513 A1 describes a monitoring device, wherein the impedance between two electrodes disposed on the arterial and venous hose line is measured. A drawback is that the known devices require the creation of an electrical connection to the fluid flowing in the hose lines.

Monitoring devices which can detect the outflow of blood at the puncture point are described in International Patent Publication No. WO 2006/008866 A1 and U.S. Patent Publication No. 2005/0038325 A1. These devices comprise a moisture sensor.

Various methods are known for determining the concentration of specific components in a patient's blood, for example for determining the concentration of haemoglobin in the blood or the haematocrit. Methods are known for measuring the concentration of blood constituents, which require the taking of a blood sample. Measuring methods are however also known, wherein the concentration of constituents in the blood flowing through a hose line is measured non-invasively. These methods are used especially when, in an extracorporeal blood treatment, the blood flows through the hose line of an extracorporeal blood circuit.

International Patent Publication No. WO 2008/000433 A1 describes a method and a device for determining the concentration of specific blood constituents in a blood-filled transparent hose line of an extracorporeal blood circuit of an extracorporeal blood treatment apparatus. The known method and the known device permit in particular the determination of the haemoglobin concentration and the proportion of red blood corpuscles (erythrocytes) in the total volume of the blood. During the measurement, the hose line is clamped between two parallel contact faces. The measurement of the haemoglobin concentration or the haematocrit is based on the scattering or transmission of electromagnetic radiation in the blood. With a light emitter, light of a specific wavelength is coupled through the transparent hose line into the blood, whereas with a light detector the scattered or transmitted light is measured. The haematocrit is then determined from the ratio of the intensity of the light entering into the blood and exiting from the blood.

In extracorporeal blood treatment methods, for example haemodialysis, haemofiltration and haemodiafiltration, an arteriovenous fistula is often applied surgically as an access to the patient's blood vessel system. The use of an implant is also possible. When mention is made below of a "fistula," this is understood to mean any kind of connection between a vein and an artery to create a vascular access.

In the period free from dialysis, the blood flow in the fistula corresponds to a functional left/right shunt, wherein a part of the arterial blood is fed from the heart minute volume (HMV), bypassing a peripheral use, directly to the venous system and the heart. The fistula flow recirculates via the heart and lungs. The fractional part of the fistula flow in the heart minute volume is defined as the cardiopulmonary recirculation. During the dialysis treatment, the blood emitted from the left ventricle of the heart for the most part flows into the capillary systems of all the organs and to a small extent into the fistula. In the case where the blood flow in the extracorporeal blood circuit is smaller than the flow of the blood flowing into the fistula or out of the fistula, a part of the fistula blood flows through the extracorporeal blood circuit and the other part through the fistula. The extracorporeal blood, the blood flowing through the fistula and the blood coming from the capillary systems finally unite again in the return flow to the heart. If, on the other hand, the extracorporeal blood flow is greater than the fistula flow, blood from the extracorporeal blood circuit recirculates, a flow passing through the fistula from the venous to the arterial connection.

A method and a device for determining the recirculation in a fistula or the cardiopulmonary recirculation are described in International Patent Publication No. WO 2009/065611 A1. The known method and the known device are based on the fact that the sum of the fistula recirculation ($R_A$) and the cardiopulmonary recirculation part ($R_{CP}$), i.e., the total recirculation (R), is determined for two different blood flow rates.

International Patent Publication No. WO 2009/065611 A1 also describes the theoretical background to the effect of the fistula recirculation and cardiopulmonary recirculation. These effects are also described in the technical article "Automatic Measurement of Recirculation" by Krämer and Polaschegg, EDTNA-ERCA Journal, Vol. XIX, No. 3 (1993).

SUMMARY

A problem underlying the present invention is to monitor, with a high degree of reliability, the access to a patient's vessel without extensive changes to the blood treatment apparatus and without the use of separate components.

A device according to the present invention and a method according to the present invention are based on the monitoring of a characteristic property of the blood flowing in the arterial blood line of the extracorporeal blood circuit, in particular the concentration of haemoglobin in the blood flowing in the extracorporeal blood circuit.

In the case of an incorrect vascular access, the flow conditions change in the communicating intra- and extracorporeal blood circulation system. These changes in the flow conditions can be detected as a change in a blood parameter. It is sufficient if only a single blood parameter is monitored. In order to increase the reliability of the measurement according to the present invention, however, a number of blood parameters can also be monitored, it being concluded that there is an incorrect vascular access when all the monitored blood parameters change.

It is advantageous for the device according to the present invention and the method according to the present invention that the measurement of the characteristic property of the blood takes place in or on the arterial blood line; i.e., between dialyser and arterial cannula.

In the case of a patient without a fistula, the total blood flows through the path via the heart and lungs and all the capillary systems of the internal organs, the muscles and skin, etc., then flowing back again to the heart. In the case of a patient on dialysis with a fistula, a part of the circulating blood no longer flows through the capillary systems, but bypasses the latter and takes the path via the fistula applied in parallel to the capillary systems. This so-called "cardiopulmonary recirculation" is always present in the case of a patient with a fistula, and more precisely both during a dialysis treatment and when the patient is not connected to an extracorporeal blood circuit. Accordingly, when an extracorporeal blood circuit is connected, a part of the blood treated in the dialyser and fed back into the fistula via the venous needle is conveyed directly via heart and lungs back into the fistula, bypassing the capillary systems. This cardiopulmonary recirculation is always present and unavoidable. Independently of the cardiopulmonary recirculation, in the case of a possible occurrence of a fistula recirculation in the fistula, a part of the treated blood fed back into the fistula via the venous cannula can also enter again into the arterial cannula on this direct path.

Both recirculation processes have an effect on the measured values of the various blood parameters in the arterial line. In the event of the venous needle being pulled out of the fistula, the freshly treated blood flowing in the venous blood line suddenly no longer passes into the fistula. On the one hand, the admixture of already treated blood via the short-circuit path of the possibly present fistula recirculation into the arterial line is consequently absent and, on the other hand, the admixture of freshly treated blood via the bypass of the cardiopulmonary recirculation into the arterial line is always absent.

Downstream after the dialyser, i.e., in the venous line, the haemoglobin concentration, the haematocrit concentration and the viscosity, for example, are increased during dialysis due to the water extraction in the dialyser compared to the corresponding measured values in the arterial line, i.e., an increase in concentration takes place in the dialyser. In the case of a venous needle disconnection, the absence of the admixture of more highly concentrated blood into the fistula on the arterial side leads to a reduction in the corresponding measured values.

It has been shown that, in the event of a venous needle disconnection, the admixture of blood already treated in the dialyser via the paths of the cardiopulmonary recirculation and the possibly present fistula recirculation into the arterial blood line is absent. In the event of a venous needle disconnection, therefore, the change in the various blood parameters in the arterial blood line of the extracorporeal blood circuit can be detected. Since the cardiopulmonary recirculation is always present, monitoring of the patient access is possible even when a fistula recirculation is not present.

In principle, all blood parameters can be used as measured variables that lead either to a detectable increase or decrease in the parameter in the arterial blood line. The blood parameter can be a parameter from the list comprising haemoglobin concentration, haematocrit, viscosity, oxygen saturation, temperature, pH value, ion concentration, for example at least one ion concentration from: Na+, Cl−, Ca++, K, Mg++, bicarbonate concentration or glucose concentration.

It can be concluded that there is a venous needle disconnection if a reduction in the corresponding measured value of a monitored blood parameter is measured in the arterial blood line of the extracorporeal blood circuit, wherein the corresponding value of the same blood parameter at a point after the dialyser, assuming a fault-free vascular access, is greater than it is before the dialyser.

Similarly, it can be concluded that there is a venous needle disconnection if an increase in the corresponding measured value of a monitored blood parameter is measured in the arterial blood line of the extracorporeal blood circuit, wherein the corresponding value of the same blood parameter at a point after the dialyser, assuming a fault-free vascular access, is less than it is before the dialyser.

Accordingly, blood parameters whose measured values display different amounts before and after the dialyser are suitable for the monitoring of a venous needle disconnection according to the present invention.

A change in the blood parameter in the dialyser can occur, for example, due to a "thickening" of the blood due to water extraction in the dialyser on account of ultrafiltration. The existing heat transfer between the blood side and dialysate side can however also lead to a change in the parameter.

The behaviour of, for example, the blood temperature as a possible blood parameter in the extracorporeal blood circuit depends on the heating regime on the dialysate side. In the case where a slight amount of heat is extracted from the blood in the dialyser, the blood temperature in the case of a fault-free vascular access lies, downstream of the dialyser, slightly below the corresponding temperature on the arterial side. Accordingly, cooler blood is admixed in the fistula and conveyed into the arterial line via the routes of the cardiopulmonary recirculation and the fistula recirculation. The admixture of cooler blood into the arterial line is absent in the event of a venous needle disconnection, which leads to a measurable increase in temperature there. In the reverse case, where a slight amount of heat is fed to the blood in the dialyser, a venous needle disconnection can be detected by a drop in the blood temperature in the arterial line, because then the admixture of warmer blood into the arterial line is absent.

The measurement of the haemoglobin concentration has the advantage that use can be made of the methods known in the prior art with which the haemoglobin concentration can be rapidly determined. All measuring methods for determining the haemoglobin concentration can in principle be used. To advantage, the known optical methods are used. The haemoglobin concentration can however also be determined by means of the known ultrasound methods. It is advantageous if the measurement of the haemoglobin concentration takes place non-invasively.

The device according to the present invention for monitoring the patient access comprises a measuring unit configured for measuring the haemoglobin concentration in the blood flowing in the arterial blood line of the extracorporeal blood circuit and a control and computing unit, which is designed such that it is concluded that there is an incorrect vascular access if there is a reduction in the haemoglobin concentration by an amount which exceeds a preset amount. The reduction in the haemoglobin concentration by an amount which exceeds a preset amount can be established by various mathematical evaluation methods.

In a preferred exemplary embodiment of the present invention, the control and computing unit comprises a comparison unit configured for comparing the measured haemoglobin concentration with a preset threshold value and a generation unit configured for generating a control signal if the amount of the difference between the measured haemoglobin concentration and the preset threshold value is greater than zero.

In an alternative preferred exemplary embodiment, the control and computing unit comprises a comparison unit configured for comparing the first haemoglobin concentration measured at a first preceding time with a second haemoglobin concentration measured at a second subsequent time. The control signal is generated if the amount of the difference between the first and second haemoglobin concentration is greater than a preset threshold value. It is advantageous that, even if there is a change in the haemoglobin concentration due to other circumstances, the reduction in the haemoglobin concentration due to a needle disconnection can be detected with a high degree of reliability, if the time interval between the two measurements is selected to be so short that, within the time interval, a change in the haemoglobin concentration due to other circumstances is not to be expected. For example, the measurements should take place at two points in time, between which the blood flow rate and/or the ultrafiltration rate is not changed. The measurements at the two successive points in time preferably take place during the whole blood treatment.

In order to increase the reliability of the measuring method according to the present invention, the cardiopulmonary recirculation can be measured and compared with a preset upper and lower threshold value, it then being concluded, in the case of a reduction in the haemoglobin concentration by an amount which exceeds a preset amount, that there is an incorrect vascular access if the measured cardiopulmonary recirculation lies between the preset upper and lower threshold value. Instead of a value range, however, it is also possible to set just an upper or a lower threshold value for the comparison of the measured cardiopulmonary recirculation.

A further preferred exemplary embodiment of the monitoring device according to the present invention provides for an alarm unit, which emits an acoustic, optical and/or tactile alarm when the control and computing unit establishes an incorrect vascular access.

The apparatus for extracorporeal blood treatment according to the present invention comprises the device according to the present invention for monitoring the vascular access. It is advantageous that the device according to the present invention and the method according to the present invention do not make use of external components which require additional manipulations or unnecessarily restrict the patient's freedom of movement.

A preferred exemplary embodiment of the blood treatment apparatus according to the present invention makes provision such that the control unit of the blood treatment apparatus undertakes an intervention into the machine control if the control and computing unit of the monitoring device generates a control signal when there is an incorrect vascular access. The control unit is preferably designed such that the blood pump disposed in the extracorporeal blood circuit is stopped as an intervention into the machine control. Moreover, a shut-off element disposed in the venous blood line is preferably closed. This effectively prevents blood from passing into the surroundings in the event of an incorrect vascular access, for example when the venous puncture cannula has slipped out or there is a leakage in the hose system.

Exemplary embodiments of the present invention are explained below in greater detail with reference to the accompanying drawings.

DETAILED DESCRIPTION

The device according to the present invention for monitoring a vascular access can form a separate unit or can also be a component part of the extracorporeal blood treatment apparatus. If the monitoring device according to the present invention is a component part of the blood treatment apparatus, the monitoring device according to the present invention can make use of specific subassemblies or components which are in any case present in the blood treatment apparatus.

Figure 1:
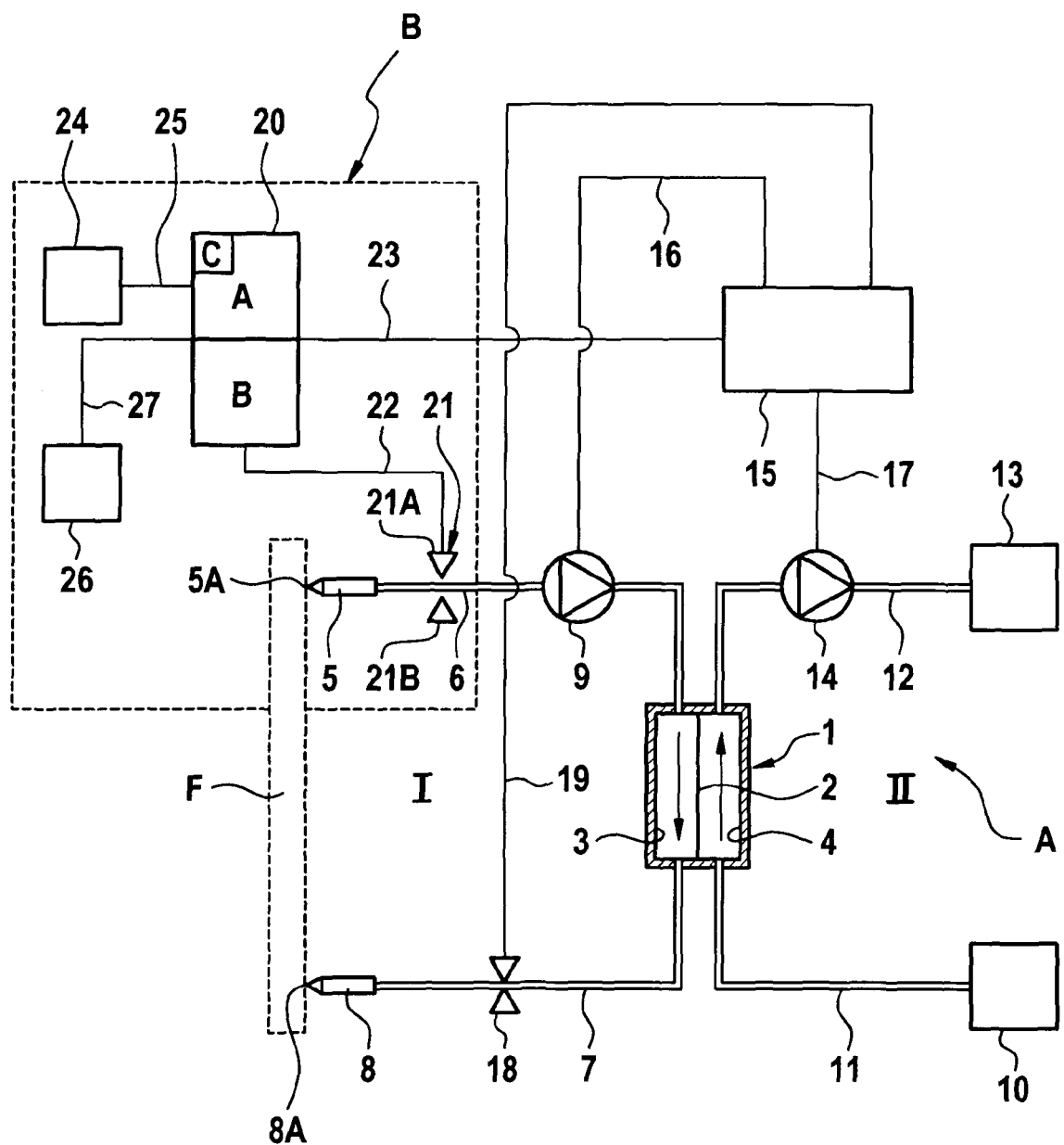
FIG. 1 shows, in a simplified schematic representation, the main components of an extracorporeal blood treatment apparatus according to the present invention with a device according to the present invention for monitoring a vascular access.

An extracorporeal blood treatment apparatus A is described below, which comprises a device B for monitoring the vascular access. FIG. 1 shows only the main components of the blood treatment apparatus in a schematic representation, since blood treatment apparatuses, for example haemodialysis apparatuses, haemofiltration apparatuses or haemodiafiltration apparatuses, are known as such to the person skilled in the art.

The blood treatment apparatus is a known haemodialysis apparatus, which comprises a dialyser 1 which is divided by a semi-permeable membrane 2 into a blood chamber 3 and a dialysing fluid chamber 4. Connected by an arterial puncture cannula 5 to arterial part 5A of a fistula F of the patient is an arterial hose line 6 which leads to the inlet of blood chamber 3 of the dialyser. Leading away from the outlet of blood chamber 3 of the dialyser is a venous hose line 7, which is connected by a venous puncture cannula 8 to venous part 8A of fistula F. The blood is conveyed in extracorporeal blood circuit I by a blood pump 9, which is provided on arterial hose line 6.

Dialysing fluid circuit II of the haemodialysis apparatus comprises a dialysing fluid source 10, to which dialysing fluid supply line 11 is connected, which leads to the inlet of dialysing fluid chamber 4 of the dialyser. Leading away from the outlet of dialysing fluid chamber 4 of the dialyser is a dialysing fluid discharge line 12 which leads to a drain 13. The dialysing fluid is conveyed in dialysing fluid circuit II by a dialysing fluid pump 14, which is disposed on dialysing fluid discharge line 12.

The control of the dialysis apparatus is assumed by a central control unit 15, which controls blood pump and dialysing-fluid pump 9, 14 via control lines 16, 17. Blood flow rate $Q_B$ is adjusted with blood pump 9.

Located downstream of blood chamber 3 of dialyser 1 on venous hose line 7 is an electromagnetically operated hose clamp 18, which can be opened or closed by central control unit 15 via a further control line 19. When venous hose clamp 18 is closed, the fluid flow is interrupted in extracorporeal blood circuit I, so that blood cannot pass into the surroundings.

Apart from the components shown in FIG. 1, the dialysis apparatus also comprises other subassemblies, which however for the sake of clarity are not represented. These include for example a balancing arrangement for balancing fresh and consumed dialysing fluid and an ultrafiltration device, in order to be able to withdraw fluid from the patient at a preset ultrafiltration rate $Q_{UF}$.

Device B for monitoring the venous vascular access comprises a control and computing unit 20, which is represented in FIG. 1 as a separate unit. Control and computing unit 20 can however also be a component of central control unit 15 of the blood treatment apparatus.

Moreover, monitoring device B comprises a measuring unit configured for measuring the concentration of haemoglobin in the blood flowing in the arterial blood line of extracorporeal blood circuit I. Instead of a measuring unit configured for measuring the haemoglobin concentration, a measuring unit can however also be provided for determining blood parameters other than the haemoglobin concentration. Thus, when mention is made below of haemoglobin concentration by way of example, it can also concern one or more parameters from the list comprising haemoglobin concentration, haematocrit, oxygen saturation, viscosity, temperature, pH value, ion concentration, bicarbonate concentration or glucose concentration.

The measuring unit configured for measuring haemoglobin concentration HB comprises a non-invasive optical measuring unit 21, which is disposed on arterial blood line 6 downstream of arterial puncture cannula 5 and upstream of blood pump 9. The measured values of measuring unit 21 are received by control and computing unit 20 via a data line 22. Devices for the non-invasive optical measurement of the haemoglobin concentration are known to the person skilled in the art. Instead of optical measuring devices, however, use may also be made of known devices for determining the haemoglobin concentration on the basis of an ultrasound measurement. It is irrelevant for the present invention how the haemoglobin concentration is measured.

International Patent Publication No. WO 2008/000433 A1, for example, describes a known device for measuring the haemoglobin concentration, which comprises a measuring unit 21, which comprises a light emitter 21A and a light detector 21B, in order to be able to couple and decouple light with a predetermined wavelength through arterial blood line 6 into the blood, said blood line being a transparent hose line, for example transmitting infrared light. The haemoglobin concentration is ascertained from the ratio of the intensity of the coupled and decoupled light. The assignment between the ratio of the intensity of the coupled and decoupled light and the haemoglobin concentration can be stored in a memory C of control and computing unit 20.

To measure the haemoglobin concentration, use may also be made of the optical blood volume monitor (OBVM) which is described in European Patent Application No. EP 1 748 292 A1.

In a first exemplary embodiment, control and computing unit 20 of the monitoring device comprises a comparison unit 20A configured for comparing the measured haemoglobin concentration with a preset threshold value. Moreover, control and computing unit 20 comprises a generation unit 20B configured for generating a control signal which is received by central control unit 15 via a data line 23.

A specific blood flow rate $Q_B$ and a specific ultrafiltration rate $Q_{UF}$ are set for the extracorporeal blood treatment by the doctor in charge. Central control unit 15 of the blood treatment apparatus sets speed n of centrifugal pump 9 such that the blood in extracorporeal blood circuit I is conveyed at preset flow rate $Q_B$. The ultrafiltration device (not shown) ensures that fluid is withdrawn from the patient at preset ultrafiltration rate $Q_{UF}$.

Haemoglobin concentration HB is continuously monitored during the extracorporeal blood treatment. The measured haemoglobin concentration is constantly compared with the preset threshold value in order to be able to ascertain a reduction in the haemoglobin concentration. If the amount of the difference between the measured haemoglobin concentration and the preset threshold value is greater than zero, control and computing unit 20 ascertains that an incorrect vascular access is present, i.e., the venous puncture cannula has slipped out. The preset threshold value is independent of blood flow rate $Q_B$ and ultrafiltration rate $Q_{UF}$. Different threshold values, which are assigned to different blood flow rates and ultrafiltration rates, can thus be stored in memory C of the control and computing unit, so that control and computing unit 20 can select the appropriate threshold value for instantaneous blood flow rate $Q_B$ and ultrafiltration rate $Q_{UF}$.

The threshold value for the haemoglobin concentration or another blood parameter can be a threshold value which is fixedly preset before the start or at the start of the treatment. It can however also be a dynamic threshold value which, depending on blood flow $Q_B$ and ultrafiltration rate $Q_{UF}$, is ascertained and updated continuously during the treatment or at specific time intervals. According to the present invention, the comparison of the measured value of the blood parameter then takes place with the updated threshold value. The reliability of the evaluation can thus be further improved. For the exemplary embodiment with the haemoglobin concentration as the blood parameter, the following equation then results for the calculation and updating of preset threshold value "Thresh" for the haemoglobin concentration:

$$\text{Thresh} = k \cdot HB \cdot \frac{\alpha \cdot (R_A + R_{CP})}{1 - \alpha - (R_A + R_{CP})}$$
$$= k \cdot HB \cdot \frac{\alpha \cdot R_{BTM}}{1 - \alpha - R_{BTM}}$$

$(1 > k > 0, \text{ e.g. } k = 0.5)$

Here, $R_A$ is the recirculation in the fistula and $R_{CP}$ is the cardiopulmonary recirculation part in the extracorporeal blood circuit. $R_{BTM}$ is the total recirculation measured during the dialysis. The total recirculation can be measured with a measuring device known to the person skilled in the art. Such a measuring device is described, for example, in International Patent Publication No. WO 2009/065611 A1. This measuring device 26, which is a component part of the known dialysis apparatuses, is shown only by way of indication in FIG. 1. Measuring device 26 is connected via a data line 27 to control and computing unit 20.

Monitoring device B comprises an alarm unit 24, which receives the control signal of control and computing unit 20 via a data line 25. Alarm unit 24 then emits an acoustic, optical and/or tactile alarm. The alarm unit can however also be a component part of the blood treatment apparatus. When central control unit 15 of the blood treatment apparatus receives the control signal of control and computing unit 20, central control unit 15 stops blood pump 9 immediately and immediately closes hose clamp 18, so that blood cannot pass into the surroundings.

In an alternative exemplary embodiment, the haemoglobin concentrations measured at two successive points in time are compared with one another in order to ascertain a reduction in haemoglobin concentration HB as a result of an incorrect vascular access. Comparison unit 20A of control and computing unit 20 compares first haemoglobin concentration $HB_{t1}$ measured at a first preceding time $t_1$ with a second haemoglobin concentration $HB_{t2}$ measured at a second subsequent time $t_2$. If the amount of the difference between first haemoglobin concentration $HB_{t1}$ and second haemoglobin concentration $HB_{t2}$ is greater than a preset threshold value, control and computing unit 20 generates the control signal, so that central control unit 15 of the dialysis apparatus stops blood pump 9 as an intervention into the machine control and closes venous hose clamp 18. In an alternative exemplary embodiment, it is in principle not necessary to preselect a plurality of threshold values, because, in the event of a change in the haemoglobin concentration over the whole treatment period, a sudden reduction in the haemoglobin concentration as a result of venous puncture cannula 8 slipping out can be reliably detected by the comparison of the haemoglobin concentration $HB_{t1}$ at a time $t_1$ before the slipping-out of the venous cannula and haemoglobin concentration $HB_{t2}$ at a time $t_2$ after the slipping-out of the venous cannula.

A further exemplary embodiment also provides for the monitoring of the cardiopulmonary recirculation in order to increase the reliability of the measurement.

In the normal dialysis operation with a fault-free patient access, a small partial flow of the blood fed back to the patient, which is cleaned and "thickened," does not pass continuously into the patient's capillary systems, but again passes together with untreated blood via the fistula into the arterial blood line on account of the cardiopulmonary recirculation and the possible fistula recirculation. In the event of a venous needle disconnection, therefore, "thickened" blood no longer comes onto the arterial side, but only the untreated blood from the patient. Overall, a drop in concentration can thus be measured in the arterial hose line. In order further to increase the reliability of the inventive measurement for the detection of a venous needle disconnection, it is possible to check with a measurement whether the cardiopulmonary recirculation actually lies in the expected value range.

The cardiopulmonary recirculation is measured by measuring device 26. Control and computing unit 20 compares the cardiopulmonary recirculation measured by measuring device 26 with a preset upper and lower threshold value. In the case of a reduction in the haemoglobin concentration by an amount which exceeds a preset amount, the control and computing unit in this exemplary embodiment generates a control signal only when the measured cardiopulmonary recirculation lies between the preset upper and lower threshold value.

The theoretical background to the reduction in the haemoglobin concentration as a result of the slipping-out of venous puncture cannula 8 is explained in detail below.

The slipping-out of venous puncture cannula 8 leads to an interruption of extracorporeal blood circuit I, so that the admixture of blood with a raised haemoglobin concentration via the paths of the cardiopulmonary recirculation and possible fistula recirculation into the arterial blood line is absent. This causes a drop in the haemoglobin concentration (ΔHB) in arterial blood line 6, which is detected by monitoring device B according to the present invention.

The haematocrit at arterial puncture cannula 8 is calculated from:

$$Hct_A = Hct \cdot (1-R) + Hct_V \cdot R \quad (1)$$

With $Hct_V = Hct_A/(1-\alpha)$ and $\alpha = Q_{UF}/Q_B$, the following results:

$$Hct_A = Hct \cdot (1-R) \cdot \frac{1-\alpha}{1-\alpha-R} \quad (2)$$

After a transformation and insertion of $R = R_A + R_{cp}$, the following results:

$$\frac{Hct_A - Hct}{Hct} = \frac{\alpha \cdot (R_A + R_{CP})}{1 - \alpha - (R + R_{CP})} \quad (3)$$

The symbols of equations (1), (2) and (3) are shown in the following table:

| | |
|---|---|
| $Q_B$: | Blood flow |
| $Q_{UF}$: | Ultrafiltration rate |
| R: | Total recirculation |
| $R_A$: | Recirculation in the fistula |
| $R_{cp}$: | Cardiopulmonary recirculation part in the extracorporeal blood circuit |
| Hct: | Haematocrit of the dialysis patient |
| $Hct_A$: | Haematocrit at the arterial needle |
| $Hct_V$: | Haematocrit at the venous needle |
| HB: | Haemoglobin concentration in the blood |

Equation (3) represents the change in the haematocrit (ΔHct) caused by the discontinuation of the admixture of blood with raised haemoglobin concentration via the paths of the cardiopulmonary recirculation and the possible fistula recirculation into the arterial blood line.

The following computational examples show the extent of the significance of the change.

It is shown below that a slipping-out of the venous puncture cannula leads to a significant drop in the haemoglobin concentration ΔHB. In the computational example, it is assumed that recirculation $R_A$ in the fistula=2% and the cardiopulmonary recirculation part $R_{cp}$=10%. The values shown in the following table result for different blood flow rates $Q_B$ of 200 ml/min and 300 ml/min and different ultrafiltration rates from 500 to 4000 ml/h:

| $Q_B$ (ml/min) | $Q_{UF}$ (ml/h) | $R_{cp}$ | $R_A$ | ΔHct / Hct | ΔHB (g/dl) at Hct = 35% |
|---|---|---|---|---|---|
| 200 | 500 | 0.1 | 0.02 | 0.5964% | 0.0696 |
| | 1000 | 0.1 | 0.02 | 1.2552% | 0.1464 |
| | 2000 | 0.1 | 0.02 | 2.8038% | 0.3271 |
| | 4000 | 0.1 | 0.02 | 7.3170% | 0.8537 |
| 300 | 500 | 0.1 | 0.02 | 0.3912% | 0.0456 |
| | 1000 | 0.1 | 0.02 | 0.8097% | 0.0943 |
| | 2000 | 0.1 | 0.02 | 1.7341% | 0.2023 |
| | 4000 | 0.1 | 0.02 | 4.0540% | 0.4730 |

In the above table, the empirical equation ΔHB [in g/dl]= [ΔHct in %]/3 is used for the conversion of haematocrit into the haemoglobin concentration, this being a numerical value equation ("tailor-make quantity equation").

Figure 2:
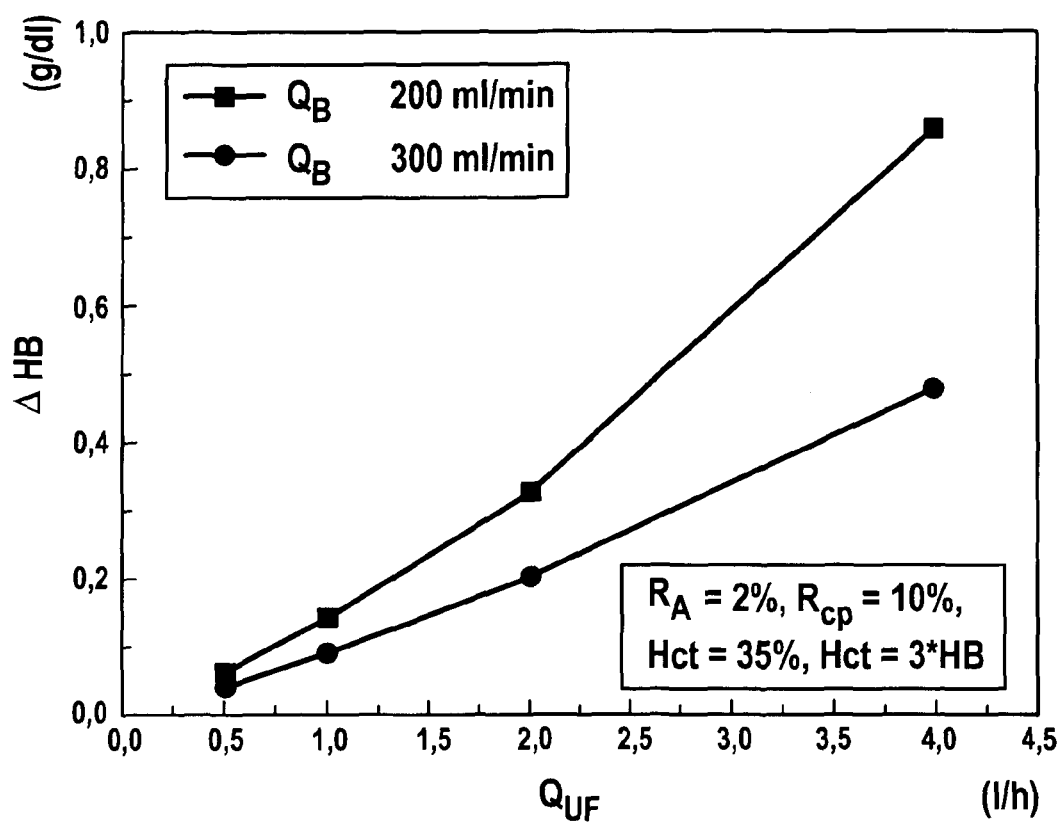
FIG. 2 shows the change in the haemoglobin concentration as a function of the ultrafiltration rate.

The above table and FIG. 2 show, for two selected constant blood flow rates $Q_B$=200 ml/min (squares) and $Q_B$=300 ml/min (circles), the quantity ΔHB of the drop in haemoglobin concentration HB in the arterial blood line due to a venous needle disconnection as a function of ultrafiltration rate $Q_{UF}$, wherein quantity ΔHB of the drop in the haemoglobin concentration becomes greater with increasing ultrafiltration rate, because the "thickening" of the cleaned blood increases with increasing ultrafiltration rate.

The invention claimed is:

1. A device for monitoring a vascular access to a patient for an extracorporeal blood treatment apparatus with an extracorporeal blood circuit, comprising an arterial blood line with an arterial puncture cannula and a venous blood line with a venous puncture cannula, wherein a blood pump for conveying blood in the extracorporeal blood circuit is disposed in one of the arterial blood line or the venous blood line, the device for monitoring the vascular access comprising:
a measuring unit configured to measure a haemoglobin concentration of the blood flowing only in the arterial blood line of the extracorporeal blood circuit; and
a control and computing unit configured to determine that there is a disconnection of the venous puncture cannula in an event of a reduction in the haemoglobin concentration of the blood flowing in the arterial blood line as measured by the measuring unit beyond a preset amount.

2. The device according to claim 1, wherein the control and computing unit comprises a comparison unit configured for comparing a measured haemoglobin concentration with a preset threshold value, and a generation unit configured for generating a control signal when a difference between the measured haemoglobin concentration and the preset threshold value is greater than zero.

3. The device according to claim 1, wherein the control and computing unit comprises a comparison unit configured to compare a first haemoglobin concentration measured at a first preceding time with a second haemoglobin concentration measured at a second subsequent time, and a generation unit configured to generate a control signal when a difference between the first haemoglobin concentration and the second haemoglobin concentration is greater than a preset threshold value.

4. The device according to claim 1, further comprising:
a measuring unit configured for measuring a cardiopulmonary recirculation, the control and computing unit comprising a comparison unit configured for comparing the measured cardiopulmonary recirculation with preset upper and lower threshold values, wherein the control and computing unit is configured to determine that there is an incorrect vascular access in the event of the reduction in the haemoglobin concentration by an amount which exceeds the preset amount, when the measured cardiopulmonary recirculation lies between the preset upper and lower threshold values.

5. The device according to claim 1, further comprising:
an alarm unit configured to emit at least one of an acoustic, optical or tactile alarm when the control and computing unit ascertains the disconnection of the venous puncture cannula.

6. The device according to claim 1, wherein the measuring unit configured to measure the haemoglobin concentration includes a measuring unit configured to non-invasively measure the haemoglobin concentration in the blood flowing in the arterial blood line.

7. An apparatus for extracorporeal blood treatment, comprising:
the device for monitoring the vascular access to the patient according to claim 1.

8. The apparatus according to claim 7, further comprising:
a central control unit configured to perform an intervention into machine control when the control and computing unit of the device for monitoring the vascular access ascertains the disconnection of the venous puncture cannula.

9. The apparatus according to claim 8, wherein the control unit of the blood treatment apparatus is configured to stop the blood pump disposed in the extracorporeal blood circuit as the intervention into the machine control.

10. The apparatus according to claim 8, wherein the control unit of the blood treatment apparatus is configured to close a shut-off element for shutting off the venous blood line of the blood treatment apparatus as the intervention into the machine control.

11. The device according to claim 1, wherein the measuring unit does not measure the hemoglobin concentration of the blood flowing in the venous blood line of the extracorporeal blood circuit.

12. The device according to claim 1, wherein the measuring unit is situated upstream of the blood pump.

13. The device according to claim 1, wherein the measuring unit is configured to measure only a single characteristic property of the blood.

14. The device according to claim 1, wherein the measuring unit is configured to measure only the haemoglobin concentration in the blood.

15. A device for monitoring a vascular access to a patient for an extracorporeal blood treatment apparatus with an extracorporeal blood circuit, comprising an arterial blood line with an arterial puncture cannula and a venous blood line with a venous puncture cannula, wherein a blood pump for conveying blood in the extracorporeal blood circuit is disposed in one of the arterial blood line or the venous blood line, the device for monitoring the vascular access comprising:
a measuring unit configured to measure a characteristic property of the blood flowing only in the arterial blood line of the extracorporeal blood circuit; and
a control and computing unit configured to determine that there is a disconnection of the venous puncture cannula in an event of a change in the characteristic property of the blood flowing in the arterial blood line as measured by the measuring unit beyond a preset amount,
wherein the control and computing unit determines the disconnection of the venous puncture cannula solely from the change in the characteristic property.

* * * * *